United States Patent [19]

Sprecker et al.

[11] Patent Number: 4,933,319

[45] Date of Patent: Jun. 12, 1990

[54] SUBSTITUTED TETRAHYDROINDANE DERIVATIVES AND ORGANOLEPTIC USES OF SUBSTITUTED TETRAHYDROINDANES

[75] Inventors: Mark A. Sprecker, Sea Bright; Robert P. Belko, Woodbridge; Charles E. J. Beck, Summit, all of N.J.

[73] Assignee: International Flavors & Fragrances Inc., New York, N.Y.

[21] Appl. No.: 424,718

[22] Filed: Oct. 20, 1989

Related U.S. Application Data

[62] Division of Ser. No. 345,014, Apr. 28, 1989, Pat. No. 4,902,840.

[51] Int. Cl.$^5$ .............................................. A61K 7/46
[52] U.S. Cl. ......................................... 512/13; 512/18; 549/545; 560/119; 562/501
[58] Field of Search ................ 512/13, 18; 549/545; 560/119; 562/501

[56] References Cited

U.S. PATENT DOCUMENTS

| | | | |
|---|---|---|---|
| 3,293,281 | 12/1966 | Dowbenko | 560/119 |
| 3,636,165 | 1/1972 | Hall | 260/617 F |
| 3,647,826 | 3/1972 | Hall | 260/348 C |
| 3,767,713 | 10/1973 | Theimer | 549/545 |
| 3,806,472 | 4/1974 | Hall | 252/522 |
| 3,876,562 | 4/1975 | Hall | 512/13 |
| 4,634,548 | 1/1987 | Helmlinger et al. | 549/545 |

Primary Examiner—James H. Reamer
Attorney, Agent, or Firm—Arthur L. Liberman

[57] ABSTRACT

Described are substituted tetrahydroindanes defined according to the generic structure:

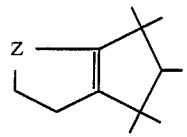

wherein Z is a moiety selected from the group consisting of:

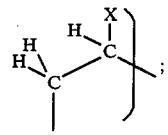

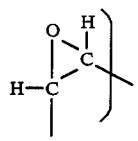

and

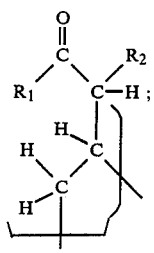

wherein X represents chloro or bromo; wherein $R_1$ represents:
—$OR_3$ or —$O^{\ominus}M^{\oplus}$;

wherein $R_3$ represents hydrogen, methyl or ethyl; wherein M represents alkali metal, sodium potassium or (Abstract continued on next page.)

lithium; wherein $R_2$ represents hydrogen or the moiety:

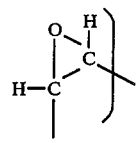

and

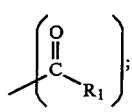

as well as uses of substituted tetrahydroindanes defined according to the structure:

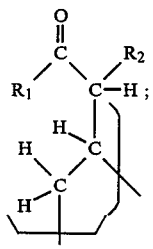

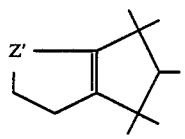

wherein Z' represents a moiety selected from the group consisting of:

wherein $R_2$ is hydrogen and wherein $R_1$ is the moiety:

—OR$_3$' wherein $R_3$' is methyl or ethyl in augmenting or enhancing the aroma of perfume compositions, colognes and perfumed articles including but not limited to perfumed polymers, solid or liquid anionic, cationic, nonionic or zwitterionic detergents, fabric softener compositions, fabric softener articles, hair preparations and cosmetic powders.

14 Claims, 7 Drawing Sheets

GC-MS PROFILE FOR EXAMPLE I.

NMR SPECTRUM FOR EXAMPLE I.

FIG.3 N.M.R. SPECTRUM FOR EXAMPLE II.

FIG. 4 NMR SPECTRUM FOR EXAMPLE II

FIG. 5 NMR SPECTRUM FOR EXAMPLE III.

SUBSTITUTED TETRAHYDROINDANE DERIVATIVES AND ORGANOLEPTIC USES OF SUBSTITUTED TETRAHYDROINDANES

This is a divisional of application Ser. No. 345,014, filed 04/28/89, now U.S. Pat. No. 4,902,840.

BACKGROUND OF THE INVENTION

This invention relates to substituted tetrahydroindanes some of which are useful lin augmenting or enhancing the aroma of perfume compositions, colognes and perfumed articles. Other substituted tetrahydroindanes of our invention are useful as intermediates in chemical processes used to synthesize compounds which are, interalia, useful in augmenting or enhancing the aroma of perfume compositions, colognes and perfumed articles.

Dry woody, rose, fruity, floral and tobacco-like aromas with date-like, fig-like, tobacco and rose topnotes are particularly desirable in augmenting or enhancing the aroma of perfume compositions, colognes and perfumed articles (e.g., solid or liquid anionic, cationic, nonionic or zwitterionic detergents, fabric softener compositions, fabric softener articles, hair preparations, cosmetic powders and perfumed polymers. Compounds having the pentamethylindane moiety are well known in the perfume art in augmenting or enhancing the aroma of perfume compositions, colognes and perfumed articles.

Thus, the compound having the structure:

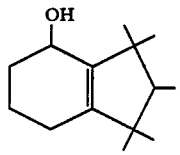

is indicated to be useful in augmenting or enhancing the aroma of perfume compositions, colognes and perfumed articles in U.S. Pat. No. 3,636,165 issued on January 18, 1972 the specification for which is incorporated by reference herein.

The compound having the structure:

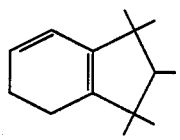

is indicated to be useful in augmenting or enhancing the aroma of perfume compositions, colognes and perfumed articles in U.S. Pat. No. 3,806,472 issued on April 23, 1974 the specification for which is incorporated by reference herein.

The compound having the structure:

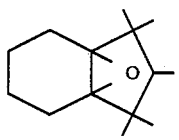

is indicated to be useful in augmenting or enhancing the aroma of perfume compositions, colognes and perfumed articles in U.S. Pat. No. 3,647,826 issued on March 7, 1972, the specification for which is incorporated by reference herein.

Nothing in the prior art discloses however the organoleptic properties of certain of the substituted tetrahydroindanes of our invention. Furthermore, nothing in the prior art discloses any of the substituted tetrahydroindanes of our invention either for their organoleptic properties or for their uses as intermediates in processes which ultimately give rise to compounds useful for their organoleptic properties.

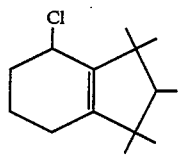

prepared according to Example I.

Figure 2:
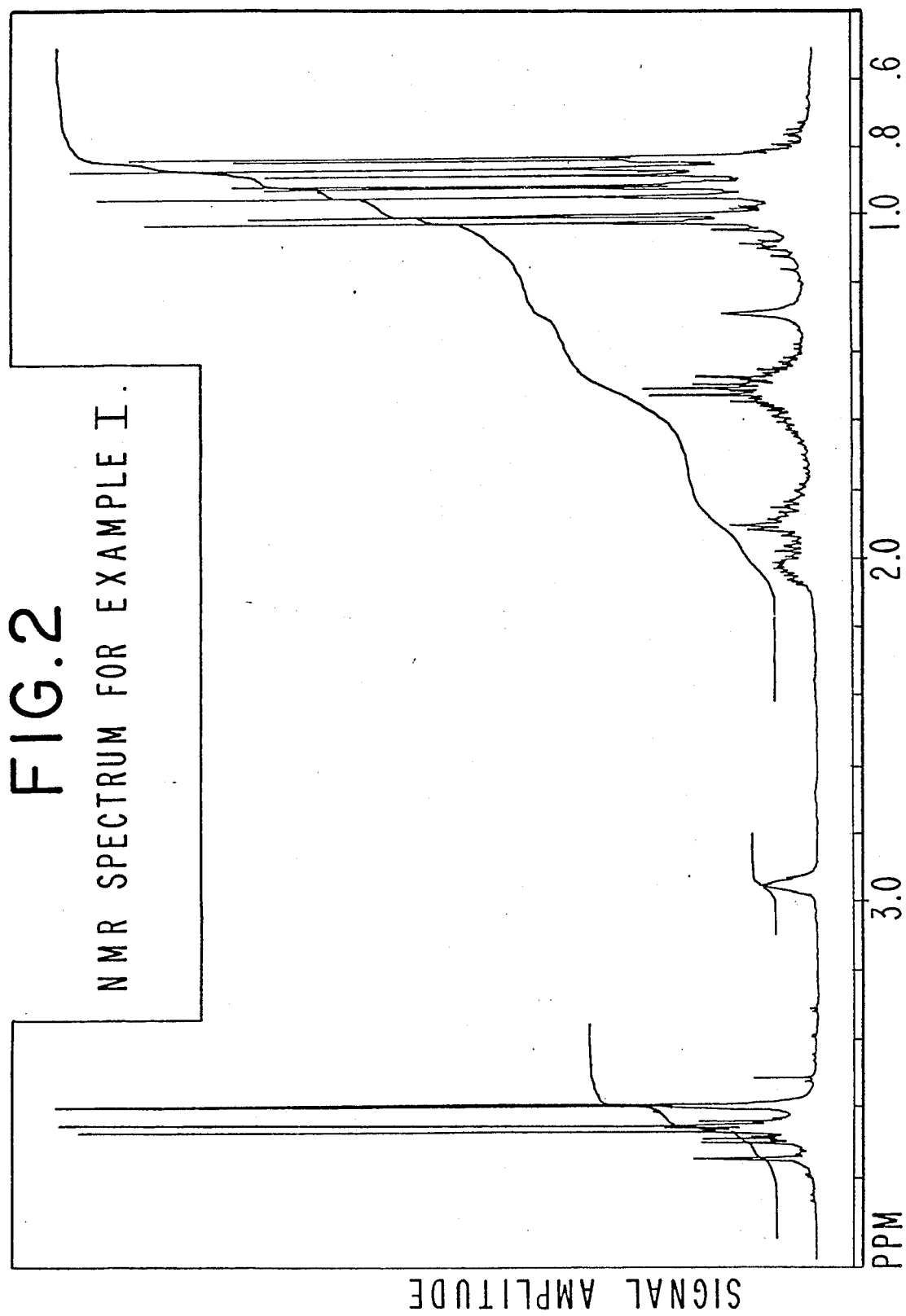

FIG. 2 is the NMR spectrum for the compound having the structure:

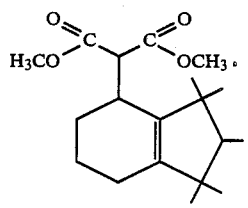

prepared according to Example II.

Figure 3:
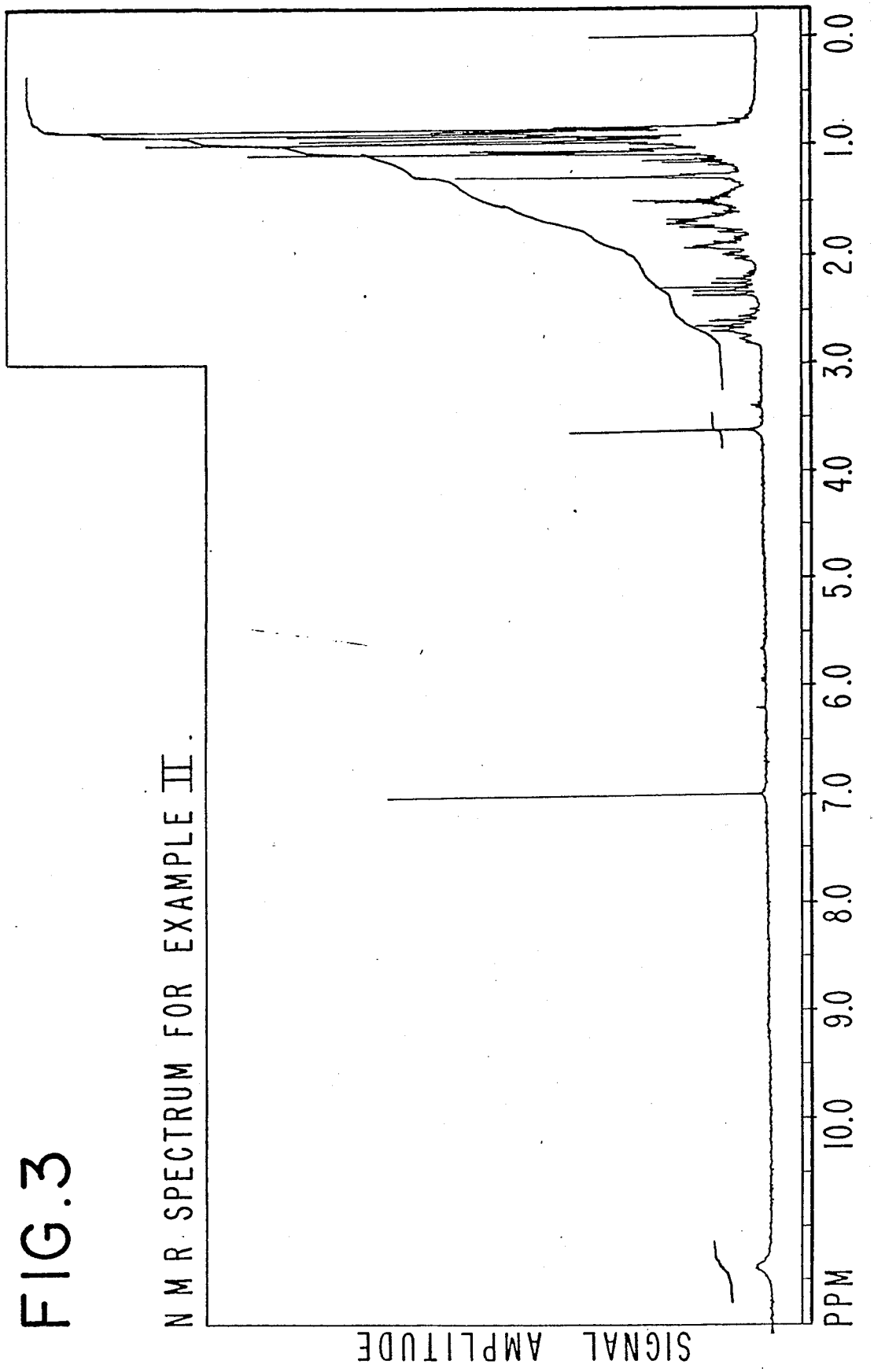

FIG. 3 is the NMR spectrum for the compound having the structure:

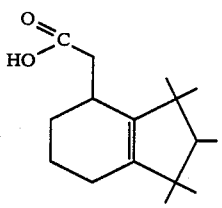

prepared according to Example II.

Figure 4:
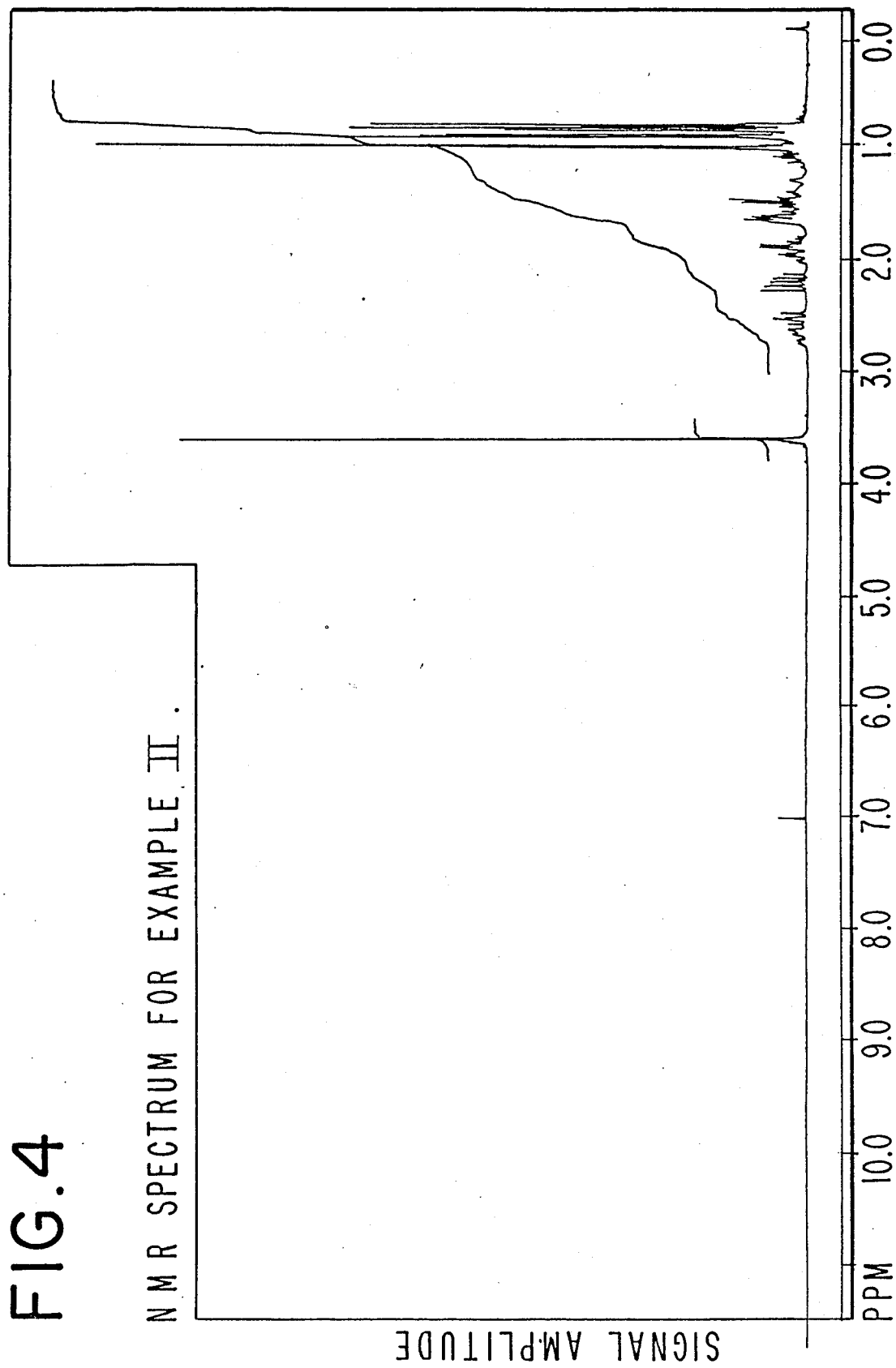

FIG. 4 is the NMR spectrum for the compound having the structure:

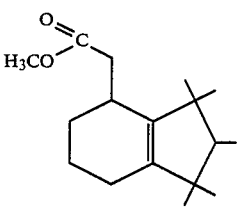

prepared according to Example II.

Figure 5:
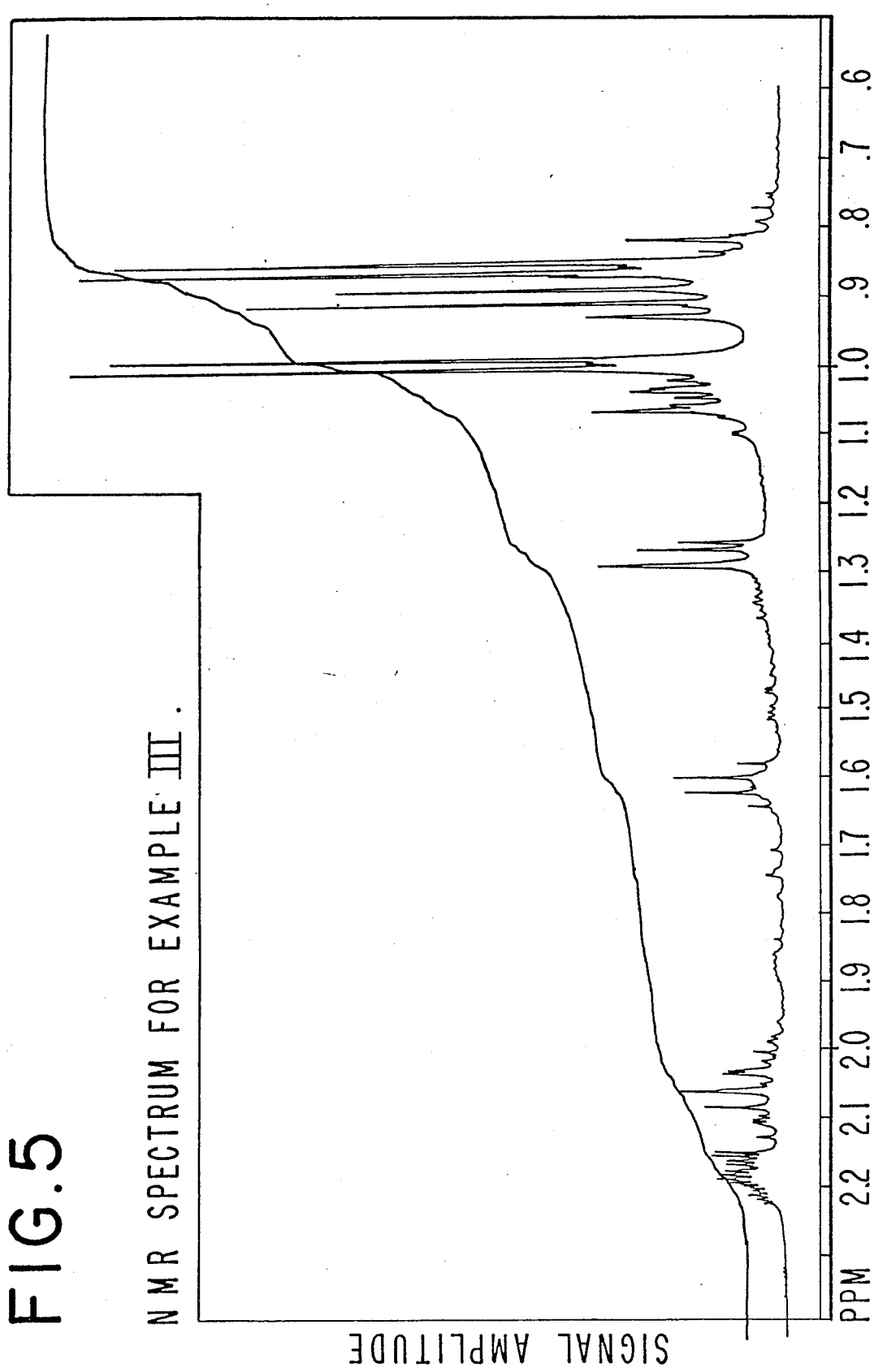

FIG. 5 is the NMR spectrum for the compound having the structure:

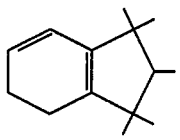

prepared according to Example III.

Figure 6:
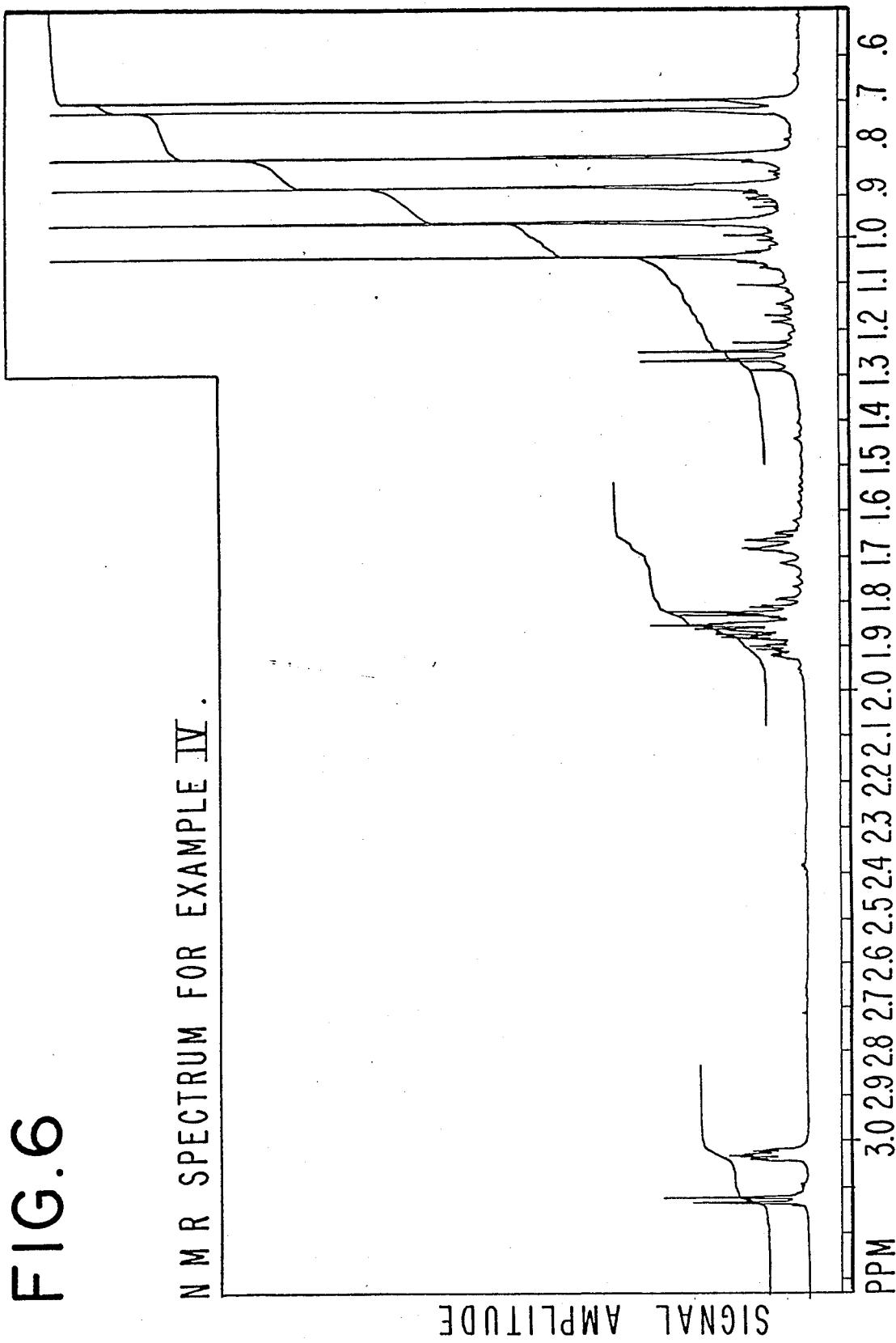

FIG. 6 is the NMR spectrum for the compound having the structure:

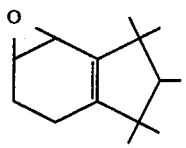

prepared according to Example IV.

Figure 7:
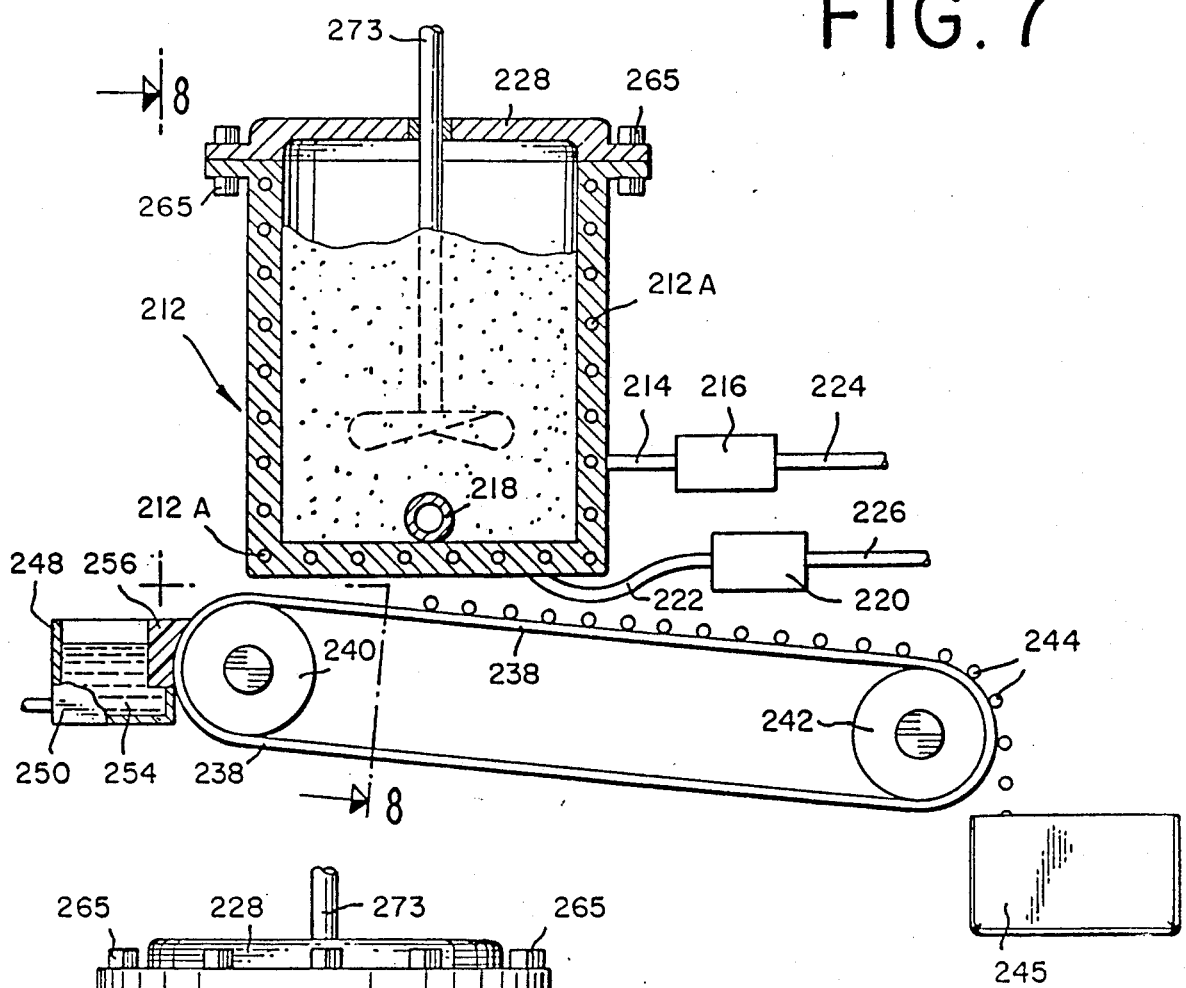

FIG. 7 is a partial side elevation and partial sectional view of an apparatus for forming polymer pellets scented with one of the perfume compositions or perfumery materials of our invention.

Figure 8:
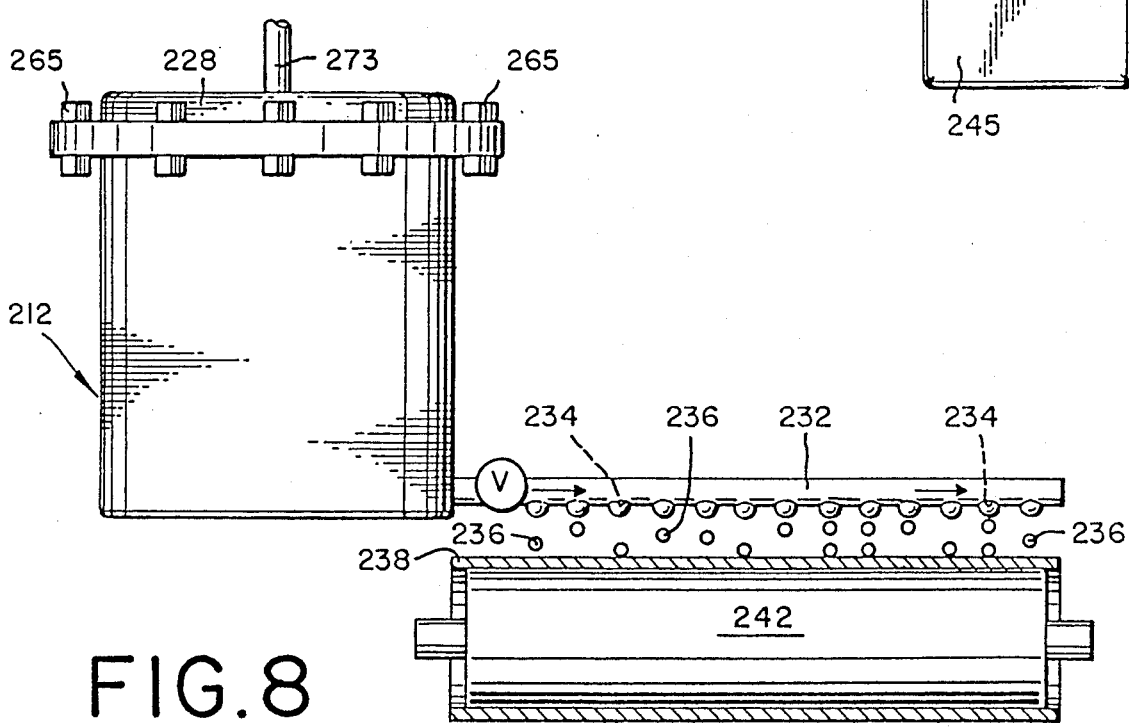

FIG. 8 is a section taken on line 8—8 of FIG. 7.

DETAILED DESCRIPTION OF THE DRAWINGS

Referring to FIGS. 7 and 8, the apparatus used in producing polymeric fragrances containing the substituted tetrahydroindanes of our invention comprises a device for forming scented polyolefin (for example) pellets which comprises a vat or container 212 into which a mixture of polyolefins such as polyethylene or an aromatic substance or scented material containing or consisting of at least one of the substituted tetrahydroindanes of our invention is placed. The container is closed by an air tight lid 228, and clamped to the container by bolts 265. A stirrer 273 traverses the lid or cover 228 in air tight manner and is rotated in a suitable manner. A surrounding cylinder 212 having heating coils 212A which are supplied with electric current through cable 224 through a rheostat or control 216 is operated to maintain the temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°–280° F. The heater is operated to maintain the upper portion of the container 212 within a temperature range of from 250°–350° F. The bottom portion of the container is heated by means of heating coils 212A heated through a control connected thereto through a connecting wire 226 to maintain the lower portion of the container within a temperature range of from 250°–350° F.

Thus, polymer (e.g., polyolefin) added to the container 212 is heated from 10–12 hours whereafter a scent or aroma imparting material which contains or consists of at least one of the substituted tetrahydroindanes of our invention is quickly added to the melt. The material must be compatible with the polyolefin and forms a homogeneous liquid melt therewith. The scented material containing at least one of the substituted tetrahydroindanes of our invention is of a type for the particular aroma desired and formulated specifically for the scenting purpose for which the polyolefin will be employed. The heat resisting coils and aromatic materials in some instances in solid or powdered form may be employed and added to the polyolefin in the container 212. Generally, about 10–30% by weight of scenting material is added to the polyolefin.

After the scent imparting material containing or consisting of at least one of the substituted tetrahydroindanes of our invention is added to the container 212, the mixture is stirred for a few minutes, for example, 5–15 minutes and maintained within the temperature ranges indicated previously by the heating coils 212A and 218. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma imparting mixture (containing at least one of the substituted tetrahydroindanes of our invention) will continuously drop through orifices 234 downwardly from the conduit 232. During this time, the temperature of the polymer (e.g., polyolefin) and aroma mixture containing or consisting of at least one of the substituted tetrahydroindanes of our invention in the container 212 is accurately controlled so that a temperature in the range of from about 210°–275° F. will exist in the conduit 232. The regulation of the temperature through the control 216 and the control 220 is essential in order to insure temperature balance to provide for the continuous dropping or dripping of molten polymer (e.g., polyolefin) and scenting material containing at least one of the substituted tetrahydroindanes of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 259 which is advantageously filled with water or some other suitable cooling liquid in order to insure the rapid cooling of each of the pellets. The pellets 244 are then collected from the container 259 and utilized in a process as illustrated, infra.

A feature of this aspect of the process of our invention is in the provision for moistening the conveyor belt 238 to insure rapid formation of the solid polymer (e.g., polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 259 which is continuously fed with water 252 to maintain a level 254 for moistening a sponge element 256 which bears against the exterior surface of the belt 238.

The instant invention provides substituted tetrahydroindanes defined according the generic structure:

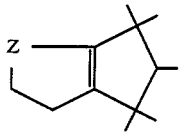

wherein Z represents a moiety selected from the group consisting of:

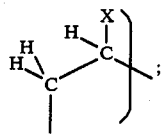

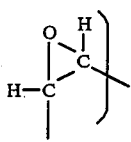

and

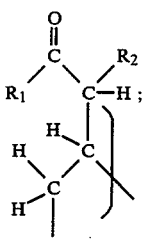

wherein X represents chloro or bromo; wherein $R_1$ represents one of the moieties:

—$OR_3$ or

—$O^{\ominus}M^{\oplus}$ wherein $R_3$ is hydrogen, methyl or ethyl; wherein M is alkali metal, sodium, potassium or lithium; wherein $R_2$ is hydrogen or the moiety:

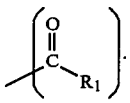

Certain of the aforementioned substituted tetrahydroindanes of our invention, to wit, those having the generic structure:

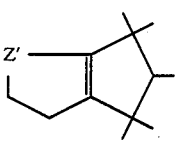

are useful in augmenting or enhancing the aroma of perfume compositions, colognes and perfumed articles (including but not limited to solid or liquid anionic, cationic, nonionic or zwitterionic detergents, perfumed polymers, fabric softener compositions and fabric softener articles, cosmetic powders, hair preparations and the like). In the case of substituted tetrahydroindanes useful in augmenting or enhancing the aroma of perfume compositions, colognes and perfumed articles, Z' is a moiety selected from the group consisting of:

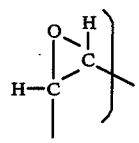

and

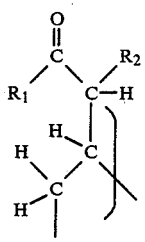

and wherein $R_2$ is hydrogen and $R_1$ is the moiety:

—$OR_3'$ wherein $R_3'$ is methyl or ethyl.

The other of the substituted tetrahydroindanes of our invention are useful as intermediates in synthesis processes for producing compounds which augment or enhance the aroma of perfume compositions, colognes or perfumed articles.

A section of our invention contemplates augmenting or enhancing the aroma of perfume compositions, colognes and perfumed articles as set forth, supra. Thus, the compounds defined according to the generic structure:

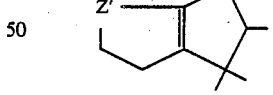

which includes the compound having the generic structure:

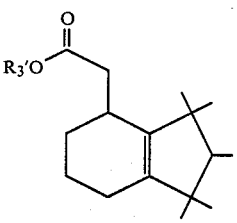

(wherein $R_3'$ is methyl or ethyl) as well as the compound having the structure:

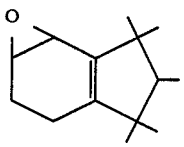

augment or enhance dry woody, rose, fruity, floral and tobacco-like aromas with date-like, fig-like, tobacco and rose topnotes.

The compounds of our invention defined according to the generic structure:

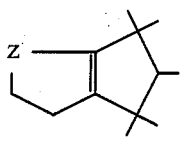

wherein Z is defined, supra, include compounds having the following structures:

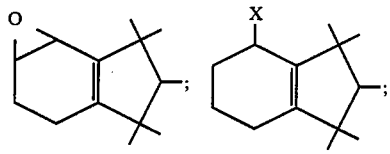

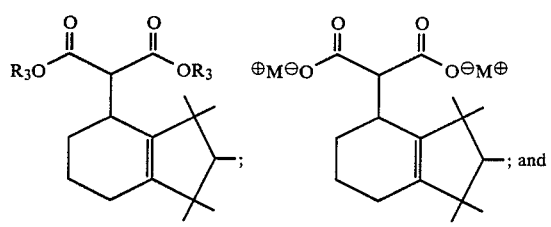

The compounds defined according to the structure:

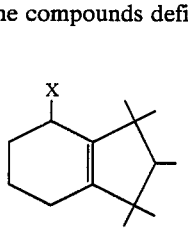

may be prepared by means of reacting the compound having the structure:

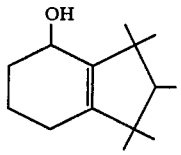

with a halogenating agent such as $SO_2Cl_2$, $SO_2Br_2$, $POCl_3$, $POBr_3$, $PCl_5$, nitrosylchloride, N-chlorosuccinimide and the like according to the reaction:

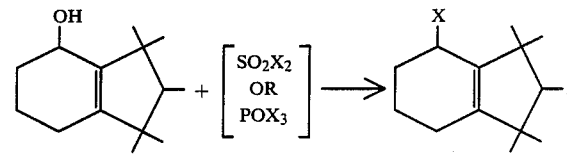

The precursor compound having the structure:

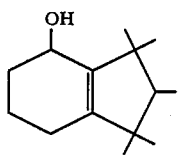

may be prepared according to Example I(c), at column 4, line 71 of U.S. Pat. No. 3,636,165 issued on January 18, 1972, the specification for which is incorporated by reference herein. The reaction is carried out in the presence of an inert solvent such as toluene at temperatures in the range of from about 50° up to about 80° C. with approximately equimolar amounts of halogenating agent and compound having the structure:

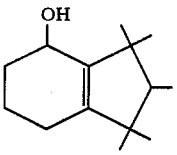

Preferably the reaction is carried out at atmospheric pressure but sub-atmospheric and super-atmospheric pressures may be used. At the end of the reaction, the reaction mass is washed with water and aqueous base (e.g., aqueous sodium bicarbonate solution). The resulting product is dried and may be used without further purification for subsequent reaction.

In preparing compounds defined according to the generic structure:

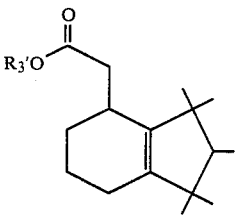

wherein $R_3'$ is methyl or ethyl (which compounds are useful for their perfumery properties in augmenting or enhancing the aroma of perfume compositions, colognes or perfumed articles), the compound having the structure:

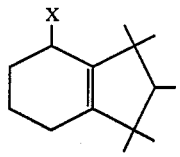

(wherein X is chloro or bromo) is first reacted with a malonic ester defined according to the structure:

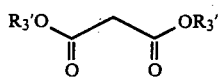

wherein $R_3'$ represents methyl or ethyl in the presence of an alcoholic solution of an alkali metal alkoxide such as a 25% solution of sodium methoxide in methanol according to the reaction:

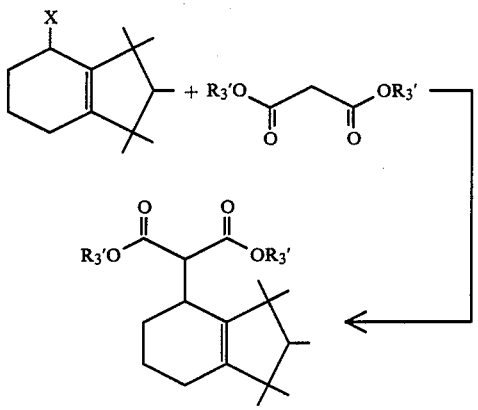

The resulting product having the structure:

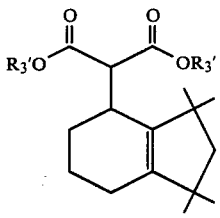

wherein $R_3'$ is methyl or ethyl is a novel chemical intermediate.

The reaction preferably takes place at ambient conditions, e.g., 20°–30° C. at atmospheric pressure. Preferably, the mole ratio of alkali metal alkoxide:malonic ester:compound having the structure:

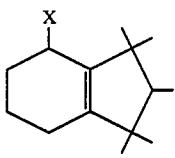

is approximately 1:1:1.

The resulting product having the structure:

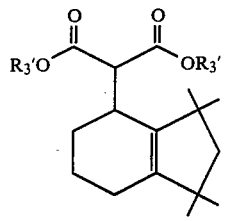

is then saponified using aqueous base, e.g., an aqueous solution of the compound having the structure:

MOH wherein M is sodium, potassium or lithium according to the reaction:

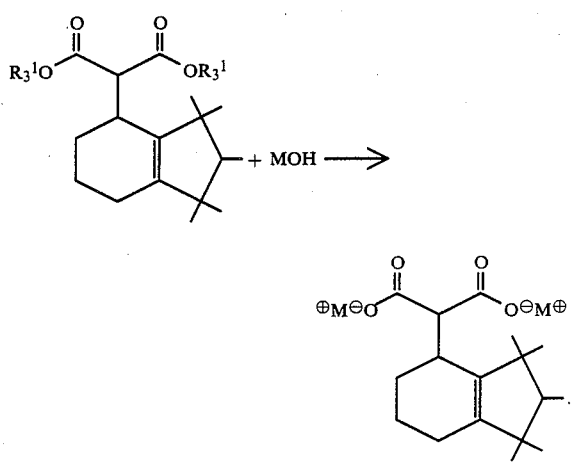

The resulting compound having the structure:

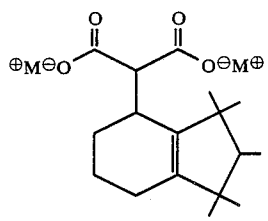

is a novel reaction intermediate. The saponification reaction takes place at reflux conditions over a period of between about one and about five hours.

The resulting salt having the structure:

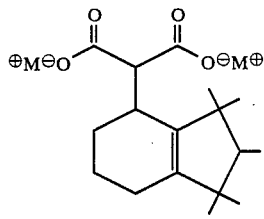

is then treated with mineral acid such as hydrochloric acid or sulfuric acid in order to form the dicarboxylic acid having the structure:

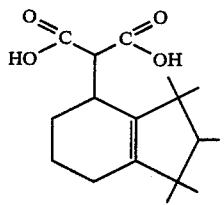

a novel chemical intermediate according to the reaction:

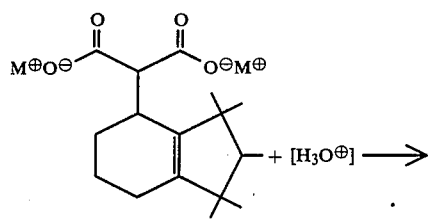

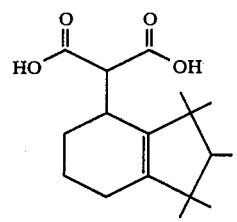

With heating, the dicarboxylic acid is monodecarboxylated to form the carboxylic acid having the structure:

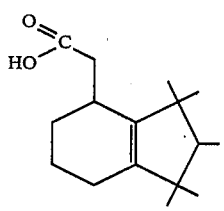

according to the reaction:

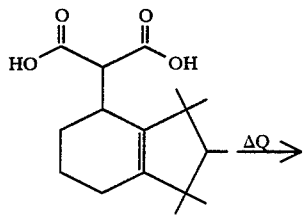

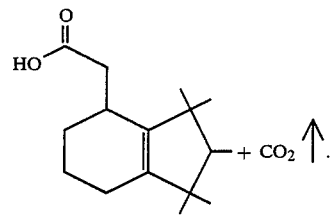

The compound having the structure:

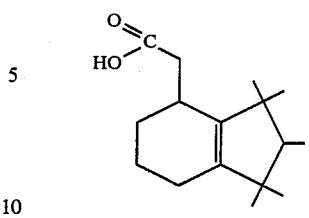

is a novel chemical intermediate.

The compound having the structure:

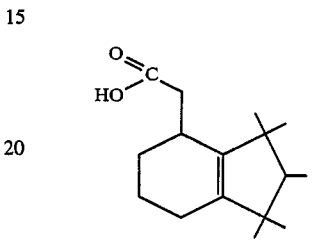

is then esterified using standard methyl or ethyl esterification conditions; for example, refluxing the compound having the structure:

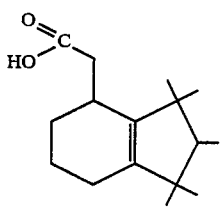

with methanol or ethanol in the presence of concentrated sulfuric acid in accordance with the reaction:

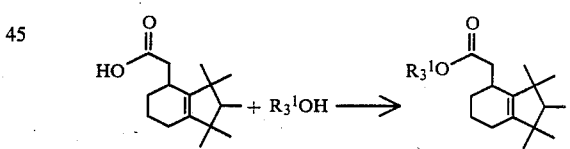

wherein $R_3'$ is methyl or ethyl.

The compound having the structure:

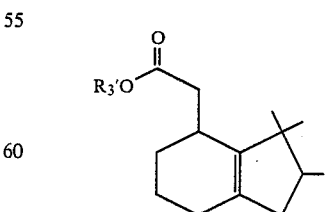

is a valuable perfumery material having properties as set forth in Table I, infra.

The compound having the structure:

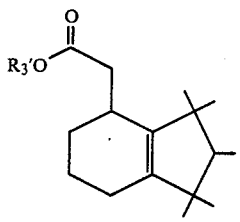

is recovered by means of fractional distillation.

The compound having the structure:

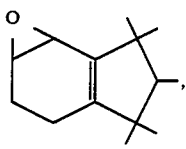

useful for its organoleptic properties in augmenting or enhancing the aroma of perfume compositions, colognes or perfumed articles is prepared by epoxidation of the compound having the structure:

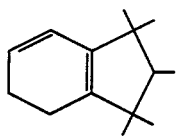

which, in turn, may be prepared by dehydrohalogenation of the compound having the structure:

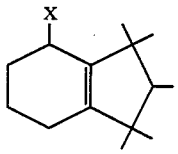

or in the alternative it may be prepared according to Example II(b) to be at line 50 of column 5 of U.S. Pat. No. 3,806,472 issued on April 23, 1974, the specification for which is incorporated herein by reference.

In carrying the dehydrohalogenation of one of the compounds defined according to the structure:

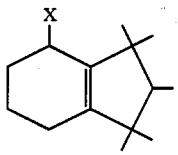

in accordance with the reaction:

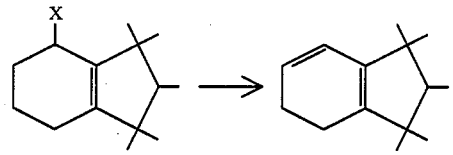

standard dehydrohalogenation procedures may be used. Thus, the reaction may be carried out using a tributyl amine dehydrohalogenation reagent at reflux conditions for a period of between about one and about four hours. The mole ratio of dehydrohalogenation reagent:compound having the structure:

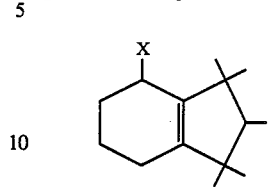

is preferably about 1:1. At the end of the reaction, the reaction mass is cooled and washed with water and weak acid and used without further purification in the epoxidation step.

In carrying out the epoxidation reaction, to wit:

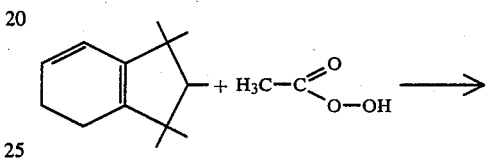

(shown using a peracetic acid epoxidation reagent, standard epoxidation reagents may be used, for example, peracetic acid as set forth in the above reaction, perbenzoic acid and the like. The epoxidation reaction is preferably carried out in the presence of an inert solvent such as toluene at a temperature in the range of from about 30° C. up to about 50° C. with the mole ratio of epoxidation reagent:hydrocarbon being preferably about 1:1. The reaction is carried out in the presence of a small amount of weak base such as sodium carbonate. At the end of the reaction, the reaction mass is quenched with water and the organic layer is washed with weak base, e.g., 5% sodium carbonate. The reaction mass is then fractionally distilled to yield the organoleptically useful compound having the structure:

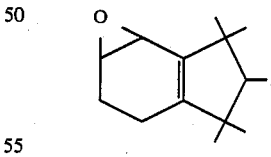

The following Table I sets forth examples of two of the substituted tetrahydroindanes useful in augmenting or enhancing the aroma of perfume compositions, perfumed articles and colognes and their organoleptic properties:

TABLE I

| Structure of Substituted Tetrahydroindane Derivatives | Perfumery Properties |
|---|---|
| The compound having the structure: | A dry woody, rose and fruity aroma profile. |

TABLE I-continued

| Structure of Substituted Tetrahydroindane Derivatives | Perfumery Properties |
|---|---|
| ![structure with H3CO-C(=O)-CH2 group on tetrahydroindane] prepared according to Example II. | |
| The compound having the structure: ![O ketone structure on tetrahydroindane] prepared according to Example IV. | A fruity, floral, tobacco-like and rose aroma with date-like, fig-like, tobacco and rose topnotes. |

One or more of the substituted tetrahydroindanes of our invention and one or more auxiliary perfume ingredients, including, for example, alcohols, aldehydes, ketones, terpinic hydrocarbons, nitriles, esters other than the substituted tetrahydroindanes of our invention, epoxides other than the substituted tetrahydroindanes of our invention, lactones, natural essential oils and synthetic essential oils, may be admixed so that the combined odors of the individual components produce a pleasant and desired fragrance, particularly and preferably in rose and tobacco fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh-smelling materials.

In perfume compositions it is the individual components which contribute to their particular olfactory characteristics, however the over-all sensory effect of the perfume composition will be at least the sum total of the effects of each of the ingredients. Thus, at least one of the substituted tetrahydroindanes of our invention can be used to alter, modify or enhance the aroma characteristics of a perfume composition, for example, by utilizing or moderating the olfactory reaction contributed by another ingredient in the composition.

The amount of one or more of the substituted tetrahydroindanes of our invention which will be effective in perfume compositions as well as in perfumed articles and colognes and perfumed polymers depends on many factors, including the other ingredients, their amounts and the effects which are desired. It has been found that perfume compositions containing as little as 0.10% of at least one of the substituted tetrahydroindanes of our invention or even less can be used to impart, augment or enhance dry woody, rose, fruity, floral and tobacco-like aromas with date-like, fig-like, tobacco and rose topnotes to soaps, cosmetics, solid or liquid anionic, cationic, nonionic or zwitterionic detergents, fabric softener compositions, fabric softener articles, hair preparations and perfumed polymers. The amount employed can range up to 100% of the fragrance components and will depend on considerations of cost, nature of the end product, the effect desired on the finished product and the particular fragrance sought.

One or more of the substituted tetrahydroindanes of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders such as talcs, dusting powders, face powders and the like. When used as (an) olfactory component(s) as little as 2% of at least one of the substituted tetrahydroindanes of our invention or even less will suffice to impart intense dry woody, rose, fruity, floral and tobacco-like aromas with date-like, fig-like, tobacco and rose topnotes to rose formulations and tobacco (perfumery) formulations. Generally, no more than 20% of at least one of the substituted tetrahydroindanes of our invention based on the ultimate end product is required in the perfume composition.

Accordingly, in perfume compositions and colognes from about 0.1% up to 100% of the perfume composition may be at least one of the substituted tetrahydroindanes of our invention. In perfumed articles, the quantity of at least one of the substituted tetrahydroindanes of our invention in the perfumed article may vary from about 0.01% up to about 25% of the perfumed article in the case of perfumed polymers, for example, and up to about 8% in the case of solid or liquid anionic, cationic, nonionic or zwitterionic detergents, for example.

In addition, the perfume composition or fragrance composition of our invention can contain a vehicle, or carrier for at least one of the substituted tetrahydroindanes of our invention. The vehicle can be a liquid such as a non-toxic alcohol, such as ethyl alcohol or a non-toxic glycol, such as propylene glycol or the like. The carrier can also be an absorbent solid, such as a gum (e.g., gum arabic, xanthan gum, or guar gum or mixtures of same) or components for encapsulating the composition (such as gelating as by means of coacervation or such as a ureaformaldehyde prepolymer when such a polymeric wall is formed around a liquid perfume composition center).

The following Examples I–IV serve to illustrate the processes for preparing the compounds of our invention and compounds useful for their organoleptic properties. Examples following Example IV (Examples V, et seq.) illustrate organoleptic utilities of the substituted tetrahydroindanes of our invention.

All parts and percentages given herein are by weight unless otherwise specified.

EXAMPLE I

Preparation of 4,5,6,7-Tetrahydro-1-chloro-1,1,2,3,3-pentamethylindane

Reaction:

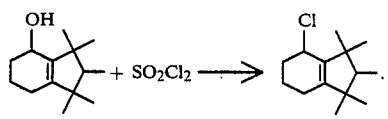

A solution of 208 grams of 4,5,6,7-tetrahydro-1-hydroxy-1,1,2,3,3-pentamethylindane in 300 grams of toluene is heated to 70° C. Thionylchloride (148.5 grams) is added dropwise at 70° C. over a period of one hour. The solution is heated to reflux eliminating SO₂ and HCl gas. The reaction mixture is cooled to 30° C. where upon it is washed with water and then 10% sodium bicarbonate. The solution is dried over 3 Å molecular sieves and used without further purification in Example II.

Figure 1:
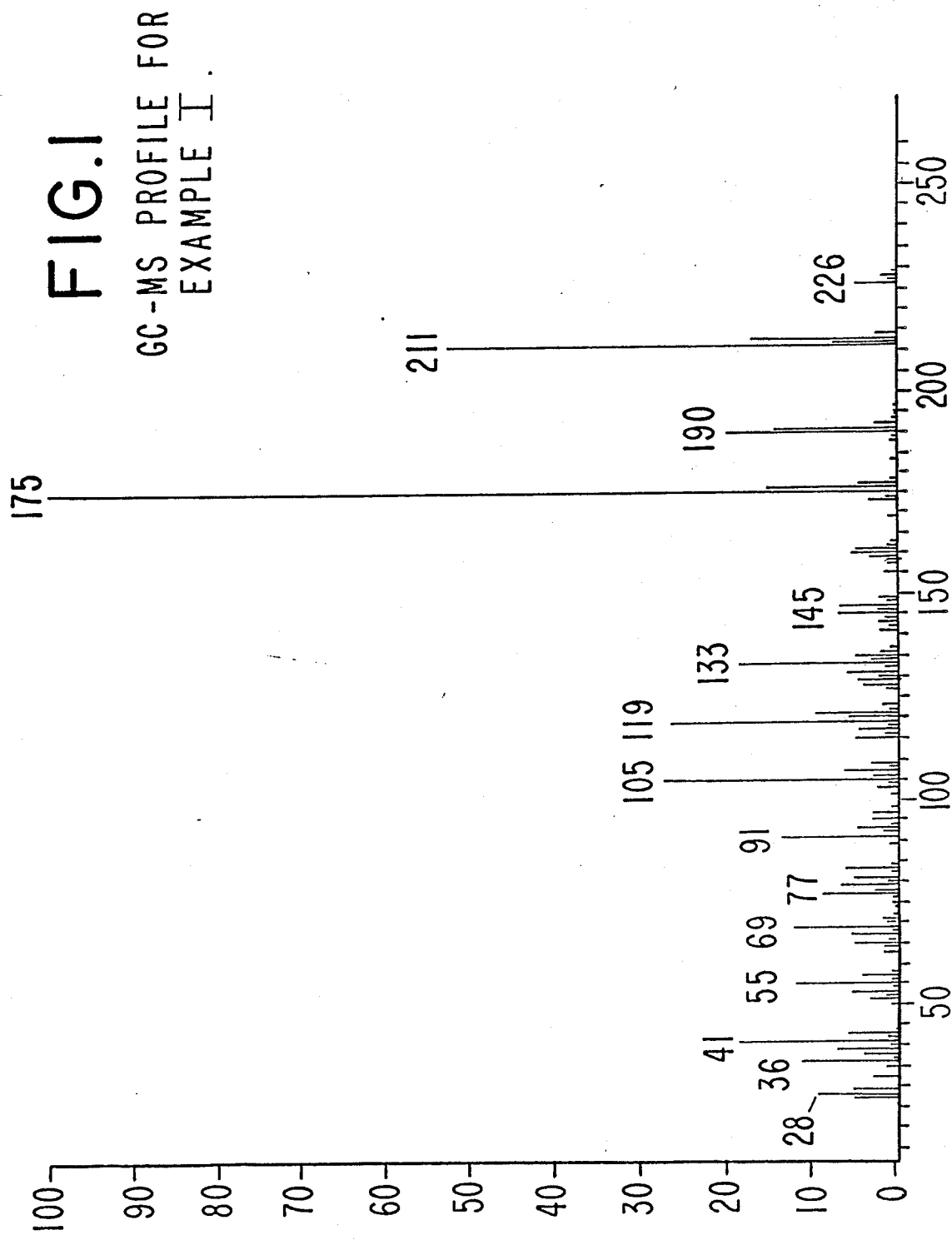
FIG. 1 is the GC-MS profile for the compound having the structure.

FIG. 1 is the GC-MS profile of the compound having the structure:

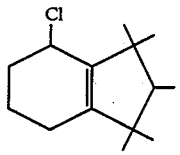

thus prepared.

EXAMPLE II

Preparation of Methyl-4,5,6,7-tetrahydro-1,1,2,3,3-pentamethyl-4-indaneacetate

Reactions:

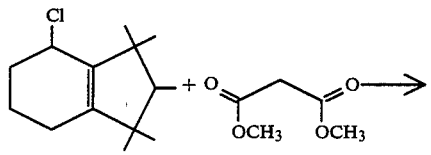 (i)

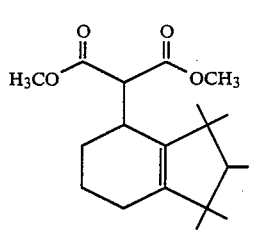

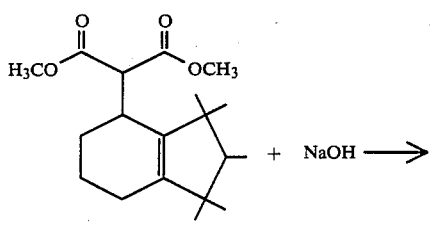 + NaOH $\longrightarrow$ (ii)

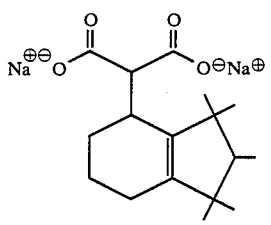

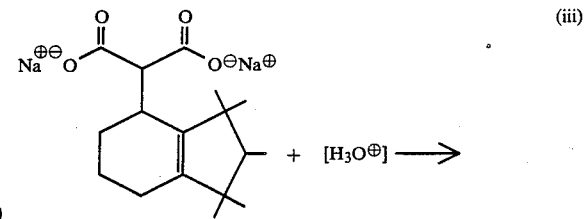 + [H₃O⁺] $\longrightarrow$ (iii)

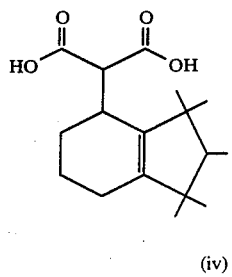

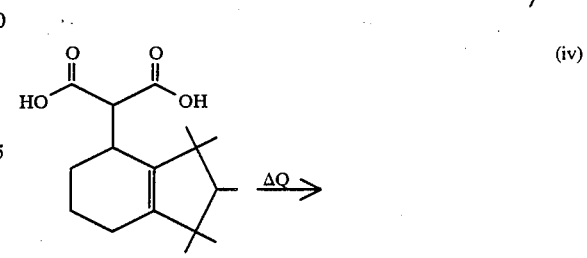 $\xrightarrow{\Delta Q}$ (iv)

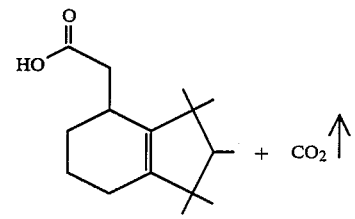 + CO₂↑ (v)

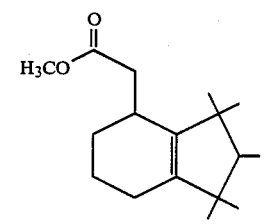 + CH₃OH $\longrightarrow$

The toluene solution of 4,5,6,7-tetrahydro-1-chloro-1,1,2,3,3-pentamethylindane (100 grams) as prepared in Example I, supra) is added to a solution of 33 grams of dimethylmalonate and 54 grams of 25% sodium methoxide in methanol over a 15 minute period at room temperature. The reaction mass is stirred two hours at room temperature and then poured into 200 ml of water. The resulting organic layer contains the compound having the structure:

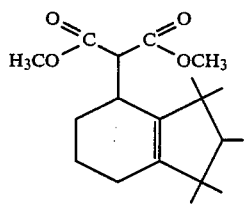

FIG. 2 is the NMR spectrum for the compound having the structure:

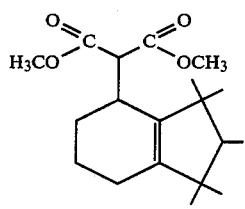

The organic layer containing the compound having the structure:

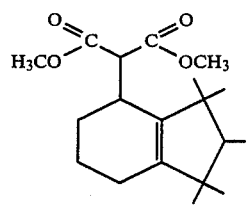

is added to 120 grams of 25% sodium hydroxide at reflux. After heating at reflux for two hours, the mixture is cooled to room temperature. The resulting product has the structure:

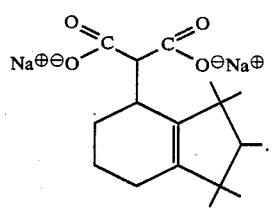

Concentrated hydrochloric acid (60 ml) is then added with stirring to effect decarboxylation forming the indanyl acetic acid derivative having the structure:

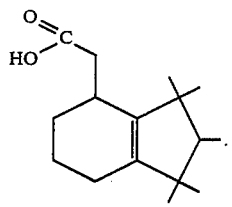

FIG. 3 is the NMR spectrum for the compound having the structure:

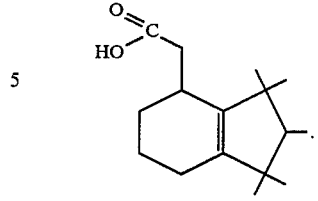

The organic layer is heated for a period of three hours at reflux in 250 ml methanol in the presence of 2 grams of concentrated sulfuric acid. Sodium bicarbonate (6 grams) is added and 200 ml of methanol are removed via atmospheric distillation.

The reaction mass is washed two times with 100 ml 5% sodium bicarbonate solution. Distillation affords 28 grams of indanyl compound having the structure:

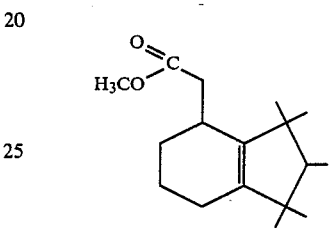

(boiling point 142° C. at 3 mm/Hg. pressure).

FIG. 4 is the NMR spectrum for the compound having the structure:

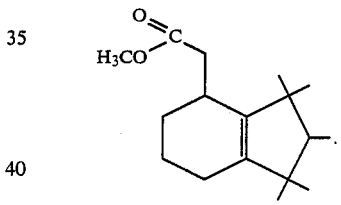

The compound having the structure:

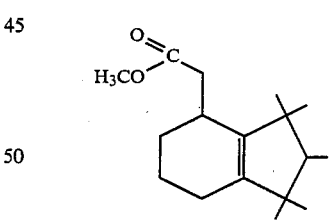

has a dry woody, rose and fruity aroma profile.

EXAMPLE III

Preparation of 6,7-Dihydro-1,2,3,4,5-pentamethyl indane

Reaction:

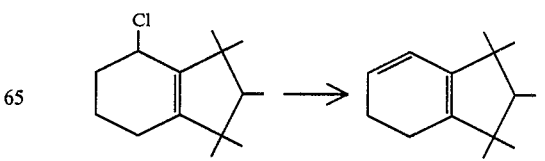

200 Grams of the toluene solution of the compound having the structure:

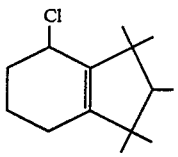

prepared according to Example I is heated for a period of two hours at reflux in the presence of 110 grams of tributyl amine. The reaction mass is cooled and wash successively with 300 ml water and 300 ml 10% acetic acid. The solution containing the compound having the structure:

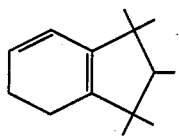

is used without further purification in Example IV, infra.

FIG. 5 is the NMR spectrum for the compound having the structure:

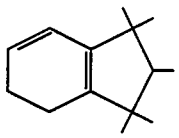

EXAMPLE IV

Preparation of 4,5-Epoxy-4,5,6,7-tetrahydro-1,1,2,3,3-pentamethylindane

Reaction:

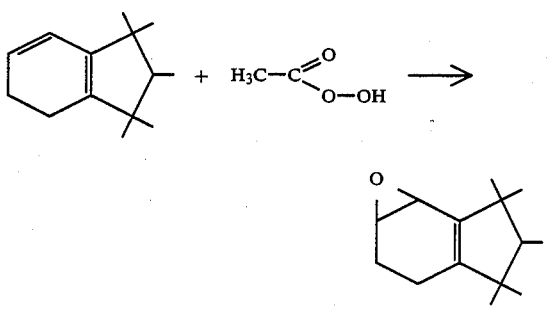

200 Grams of the toluene solution containing the compound having the structure:

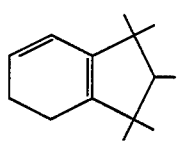

prepared according to Example III is added dropwise over a one hour period to a stirred solution of 5 grams of sodium carbonate in 146 grams of 35% peracetic acid at 40° C. The reaction mass is stirred at 40° C. for four hours; then poured into 500 ml of water. The resulting organic layer is washed successively with 200 ml of 5% sodium carbonate, 5% sodium bisulfite, and 5% sodium carbonate. Distillation affords 65 grams of the epoxide having the structure:

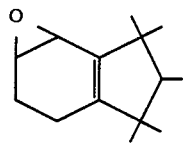

(Boiling point: 102° C. at 3 mm/Hg. pressure).

The compound having the structure:

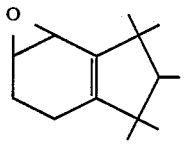

has a fruity, floral, tobacco-like and rose aroma with date-like, fig-like, tobacco and rose topnotes.

FIG. 6 is the NMR spectrum for the compound having the structure:

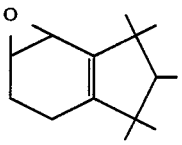

EXAMPLE V

The following rose/tobacco formulations are prepared:

| Ingredients | Parts by Weight | | |
|---|---|---|---|
| | V(A) | V(B) | V(C) |
| Phenylethyl alcohol | 12 | 12 | 12 |
| Geraniol | 14 | 14 | 14 |
| Geranyl acetate | 8 | 8 | 8 |
| Rose oxide | 4 | 4 | 4 |
| Bulgarian rose oil | 0.2 | 0.2 | 0.2 |
| Betadamascenone | 1 | 1 | 1 |
| The compound having the structure: 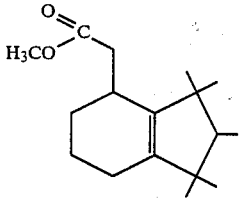 prepared according to Example II. | 18 | 0 | 0 |
| The compound having the structure: | 0 | 18 | 0 |

-continued

| Ingredients | Parts by Weight | | |
|---|---|---|---|
| | V(A) | V(B) | V(C) |

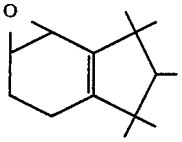

prepared according
to Example IV.
50:50 Mixture of the
compound having
the structure:            0        0        18

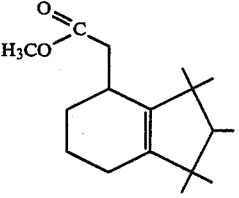

prepared according
to Example II
and the compound having
the structure:

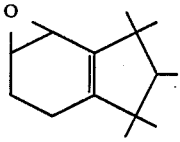

prepared according
to Example IV.

The compound having the structure:

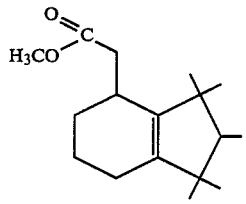

prepared according to Example II adds a dry woody and fruity undertone to this rose formulation. Accordingly, the rose formulation of Example V(A) can be described as "rose with a dry woody and fruity undertone".

The compound having the structure:

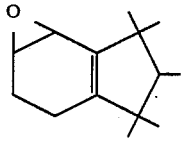

prepared according to Example IV adds to this rose formulation a fruity and tobacco-like undertone with date-like, fig-like and tobacco topnotes. Accordingly, the perfume formulation of Example V(B) can be described as "rose with fruity, floral and tobacco-like undertones and date-like, fig-like and tobacco topnotes".

The mixture of compounds having the structures:

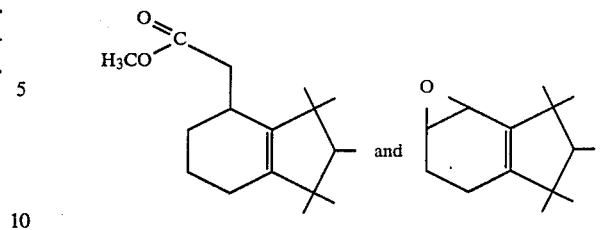

of Example V(C) adds to this rose formulation dry woody, fruity, floral and tobacco-like undertones, with date-like, fig-like and tobacco topnotes. Accordingly, the perfume composition of Example V(C) can be described as "rose with dry woody, fruity, floral and tobacco-like undertones and date-like, fig-like and tobacco topnotes".

EXAMPLE VI

Cosmetic Powder Preparation

A cosmetic powder is prepared by mixing in a ball mill 100 grams of talcum powder with 0.25 grams of one of the substances set forth in Table II below containing at least one of the substituted tetrahydroindanes of our invention. Each of the cosmetic powders has an excellent aroma as described in Table II below.

TABLE II

| Perfumery Substance | Aroma Nuance |
|---|---|
| The compound having the structure: 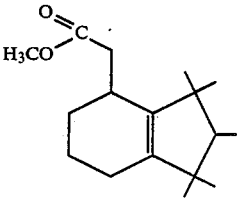 prepared according to Example II. | A dry woody, rose and fruity aroma profile. |
| The compound having the structure: 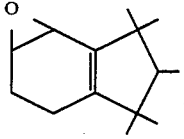 prepared according to Example IV. | A fruity, floral, tobacco-like and rose aroma with date-like, fig-like and tobacco and rose topnotes. |
| Perfume composition of Example V(A). | Rose with a dry woody and fruity undertone. |
| Perfume composition of Example V(B). | Rose with fruity, floral and tobacco-like undertones and date-like, fig-like and tobacco topnotes. |
| Perfume composition of Example V(C). | Rose with dry woody, fruity, floral and tobacco-like undertones and date-like, fig-like and tobacco topnotes. |

EXAMPLE VII

Perfumed Liquid Detergent

Concentrated liquid detergents (Lysine salt of n-dodecylbenzene sulfonic acid as more specifically described in U.S. Pat. No. 3,948,818 issued on April 6, 1976 the specification for which is incorporated by reference herein) with aromas as set forth in Table II of Example VI, supra are prepared containing 0.10%, 0.15%, 0.20%, 0.25%, 0.30% and 0.35% of each of the substances of Table II of Example VI. They are prepared by adding and homogeneously admixing the appropriate quantity of one of the substances of Table II of Example VI in the liquid detergent. The detergents all possess excellent aromas as set forth in Table II of Example VI.

EXAMPLE VIII

Preparation of a Cologne and Handkerchief Perfume

The substances set forth in Table II of Example VI are incorporated separately into colognes at concentrations of 2.0%, 2.5%, 3.0%, 3.5%, 4.0%, 4.5% and 5.0% in 75%, 80%, 85% and 90% aqueous food grade ethanol solutions; and into handkerchief perfumes at concentrations of 15%, 20%, 25% and 30%, in 80%, 85%, 90% and 95% aqueous food grade ethanol solutions. Distinctive aromas as set forth in Table II of Example VI, supra are imparted to the colognes and to the handkerchief perfume compositions at all levels indicated.

EXAMPLE IX

Preparation of Soap Composition

One hundred grams of soap chips (IVORY®, produced by the Procter & Gamble Company, of Cincinnati, Ohio) are admixed with 1 gram of each of the substances of Table II of Example VI, supra, until homogeneous compositions are obtained. The homogeneous compositions are each separated then heated under 3 atmospheres pressure at 180° C. for a period of 3 hours and the resulting liquid samples are placed in soap molds. The resulting soap cake, on cooling, manifest excellent long-lasting aromas as set forth in Table II of Example VI, supra.

EXAMPLE X

Preparation of Solid Detergent Compositions

Detergents are prepared from the following ingredients according to Example I of Canadian Letters Patent No. 1,007,948 the specification for which is incorporated by reference herein:

| Ingredients | Parts by Weight |
| --- | --- |
| NEODOL® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table II of Example VI. Each of the detergent samples has an excellent aroma as set forht in Table II of Example VI.

EXAMPLE XI

Dryer-added Fabric Softener Article

Utilizing the procedure of Example I at column 15 of U.S. Pat. No. 3,623,396, the specification for which is incorporated by reference herein, a non-woven cloth substrate useful as a dryer-added fabric softening article of manufacture is prepared wherein the substrate, the substrate coating and the outer coating and the perfuming material are as follows:

1. A water "dissolvable" paper ("Dissolyo Paper");
2. Adogen 448 (m.p. about 140° F.) as the substrate coating; and
3. An outer coating have the following formulation (m.p. about 150° F.):
   57% $C_{20-22}$ HAPS
   22% isopropyl alcohol
   20% antistatic agent
   1% of one of the substances of Table II of Example VI, supra.

Fabric softening compositions containing one of the substances of Table II of Example VI consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1:1 by weight of the substrate.

Pleasant aromas as set forth in Table II of Example VI are imparted to the head space in the dryer on operation thereof using the said drier-added softening non-woven fabric.

What is claimed is:

1. A substituted tetrahydroindane defined according to the structure:

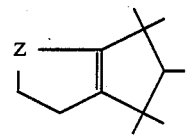

wherein Z is a moiety selected from the group consisting of:

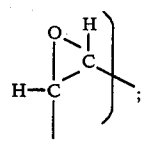

and

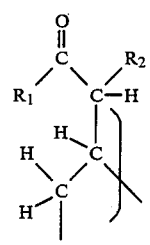

wherein $R_1$ represents a moiety selected from the group consisting of:

$-OR_3$ and $-O^{\ominus}M^{\oplus}$;

wherein $R_3$ is selected from the group consisting of hydrogen, methyl and ethyl; wherein M is alkali metal selected from the group consisting of sodium, potassium and lithium; wherein $R_2$ is selected from the group consisting of hydrogen and the moiety:

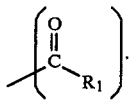

2. The substituted tetrahydroindane of claim 1 having the structure:

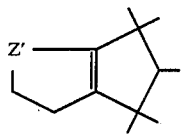

wherein Z' is a moiety selected from the group consisting of:

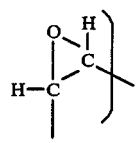

and

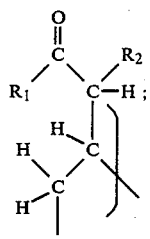

wherein $R_2$ is hydrogen; wherein $R_1$ is the moiety:

—$OR_3'$;

wherein $R_3'$ is selected from the group consisting of methyl and ethyl.

3. The compound of claim 1 having the structure:

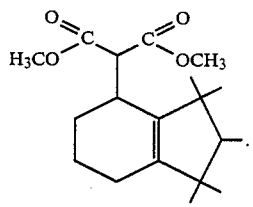

4. The compound of claim 1 having the structure:

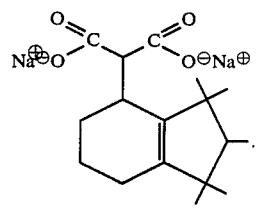

5. The compound of claim 1 having the structure:

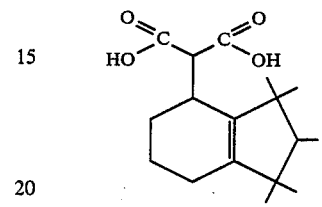

6. The compound of claim 1 having the structure:

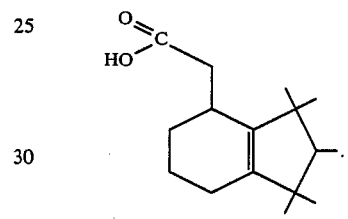

7. The compound of claim 1 having the structure:

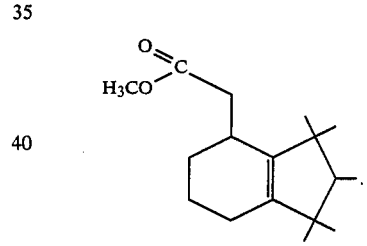

8. The compound of claim 1 having the structure:

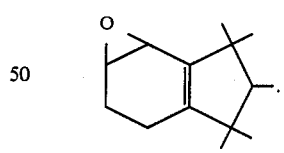

9. A process for augmenting or enhancing the aroma of a perfume composition, cologne or perfumed article comprising the step of adding to a perfume base, a cologne base or a perfumed article base, an aroma augmenting or enhancing quantity of a compound defined according to claim 2.

10. A process for augmenting or enhancing the aroma of a perfumed polymer comprising the step of adding to a polymer, an aroma augmenting or enhancing quantity of a compound defined according to claim 2.

11. A process for augmenting or enhancing the aroma of a solid or liquid anionic, cationic, nonionic or zwitterionic detergent, comprising the step of adding to a solid or liquid anionic, cationic, nonionic or zwitterionic detergent base, an aroma augmenting or enhancing compound defined according to claim 2.

12. A process for augmenting or enhancing the aroma of a perfume composition comprising the step of adding to a perfume composition, an aroma augmenting or enhancing quantity of at least one compound defined according to claim 2.

13. A process for augmenting or enhancing the aroma of a fabric softener composition or fabric softener article comprising the step of adding to a fabric softener composition or fabric softener article, an aroma augmenting or enhancing quantity of a compound defined according to claim 2.

14. A perfume composition comprising a perfume base and intmately admixed therewith, an aroma augmenting or enhancing quantity of a compound defined according to claim 2.

* * * * *